United States Patent
Gentz et al.

(10) Patent No.: US 11,291,771 B2
(45) Date of Patent: Apr. 5, 2022

(54) ELECTRONIC ADD-ON MODULE FOR INJECTION APPLIANCES

(71) Applicant: Ypsomed AG, Burgdorf (CH)

(72) Inventors: Michael Gentz, Burgdorf (CH); Ursina Streit, Schönbühl (CH); Leos Urbanek, Bern (CH); Jonas Rihs, Pieterlen (CH); Bernhard Rytz, Zollbrück (CH); Dominic Frutiger, Zürich (CH)

(73) Assignee: Ypsomed AG, Burgdorf (CH)

( * ) Notice: Subject to any disclaimer, the term of this patent is extended or adjusted under 35 U.S.C. 154(b) by 232 days.

(21) Appl. No.: 16/402,824

(22) Filed: May 3, 2019

(65) Prior Publication Data

US 2019/0255252 A1    Aug. 22, 2019

Related U.S. Application Data

(63) Continuation of application No. PCT/CH2017/050006, filed on Oct. 18, 2017.

(30) Foreign Application Priority Data

Nov. 9, 2016  (CH) .................................. 01485/16

(51) Int. Cl.
*A61M 5/20* (2006.01)
*A61M 5/315* (2006.01)

(52) U.S. Cl.
CPC .............. *A61M 5/20* (2013.01); *A61M 5/315* (2013.01); *A61M 2205/33* (2013.01);
(Continued)

(58) Field of Classification Search
CPC .... A61M 2205/332; A61M 2205/3375; A61M 5/20; A61M 5/315; A61M 5/3157; A61M 2205/3317–2205/3327; A61M 2205/52
See application file for complete search history.

(56) References Cited

U.S. PATENT DOCUMENTS 7,078,679 B2    7/2006  Westphall et al.
10,195,352 B2*  2/2019  Baran ...................... F16B 2/20
(Continued)

FOREIGN PATENT DOCUMENTS

EP    2065064 A1    6/2009
EP    2182456 A1    5/2010
(Continued)

OTHER PUBLICATIONS

Choosehandsafety.org; Feb. 14, 2016; http://choosehandsafety.org/choosing-hand-tools/hand-tool-size.*
(Continued)

*Primary Examiner* — Bhisma Mehta
*Assistant Examiner* — John J Crawford
(74) *Attorney, Agent, or Firm* — Dorsey & Whitney LLP (57) ABSTRACT

The invention relates to an electronic add-on module which is fitted releasably onto an automatic injection appliance before the start of injection. The add-on module comprises a force sensor for measuring a time-variable axial force component exerted on or transmitted to the attached add-on module by the injection appliance during an injection procedure. The add-on module also comprises a grip or a preferred grip position for gripping and holding the add-on module and the inserted injection appliance. The add-on module can additionally have a microphone for detection of acoustic signals. A state of the injection appliance can be determined by the add-on module solely on the basis of measurements of the axial force sensor, optionally supplemented by microphone measurements. The invention thus affords a straightforward and cost-effective way of monitoring or controlling the correct performance of an injection procedure carried out with an automatic injection appliance.

7 Claims, 7 Drawing Sheets

(52) U.S. Cl.
CPC .............. *A61M 2205/332* (2013.01); *A61M 2205/3317* (2013.01); *A61M 2205/43* (2013.01); *A61M 2205/52* (2013.01); *A61M 2205/583* (2013.01); *A61M 2209/00* (2013.01)

(56) References Cited

U.S. PATENT DOCUMENTS

| | | | |
|---|---|---|---|
| 2008/0169307 A1 | 7/2008 | Hofstetter | |
| 2008/0188813 A1 | 8/2008 | Miller et al. | |
| 2011/0270214 A1 | 11/2011 | Joergensen et al. | |
| 2011/0295215 A1 | 12/2011 | Nielsen et al. | |
| 2011/0313350 A1* | 12/2011 | Krulevitch | A61M 5/31525 604/65 |
| 2014/0379874 A1 | 12/2014 | Starr et al. | |
| 2015/0025470 A1* | 1/2015 | Baran | A61M 5/003 604/187 |
| 2015/0202375 A1 | 7/2015 | Schabbach et al. | |
| 2015/0273163 A1 | 10/2015 | Nielsen et al. | |
| 2015/0290396 A1* | 10/2015 | Nagar | A61M 5/3202 340/540 |
| 2016/0129182 A1* | 5/2016 | Schuster | G16H 40/63 702/56 |
| 2016/0213853 A1* | 7/2016 | Despa | A61M 5/3155 |
| 2017/0146381 A1 | 5/2017 | Eckel et al. | |
| 2018/0225560 A1 | 8/2018 | Schneider et al. | |
| 2018/0326164 A1* | 11/2018 | Bauss | A61M 5/5086 |
| 2019/0001060 A1* | 1/2019 | Gylleby | A61M 5/31568 |
| 2019/0217022 A1 | 7/2019 | Gentz et al. | |
| 2019/0365989 A1* | 12/2019 | Allerdings | A61M 5/168 |

FOREIGN PATENT DOCUMENTS

| | | | |
|---|---|---|---|
| EP | 2781230 A1 * | 9/2014 | .......... A61M 5/2033 |
| EP | 2781230 A1 | 9/2014 | |
| WO | 2010098927 A1 | 9/2010 | |
| WO | 2014023763 A1 | 2/2014 | |
| WO | 2015136564 A1 | 9/2015 | |
| WO | 2015171778 A1 | 11/2015 | |
| WO | 2015171778 A8 | 12/2015 | |
| WO | 2016102407 A1 | 6/2016 | |
| WO | 2018064784 A1 | 4/2018 | |

OTHER PUBLICATIONS

PCT, "International Preliminary Reporton Patentability", Application No. PCT/CH2017/050004, dated Apr. 9, 2019, 6 pages.

PCT, "International Search Report and Written Opinion", Application No. PCT/CH2017/050006, dated Feb. 5, 2018.

PCT, "International Search Report and Written Opinion", Application No. PCT/CH2017/050004, dated Jan. 31, 2018, 10 pages.

* cited by examiner

ELECTRONIC ADD-ON MODULE FOR INJECTION APPLIANCES

CROSS-REFERENCE TO RELATED APPLICATIONS

This application is a continuation of International Application No. PCT/CH2017/050006 filed Oct. 18, 2017, which claims priority to Swiss Application No. 01485/16 filed Nov. 9, 2016, the entire contents of all of which are incorporated by reference herein in their entirety.

FIELD OF THE INVENTION

The present invention concerns the field of medical injection appliances to administer liquid substances, in particular medicaments or medicinal substances, such as insulin and hormone preparations. The invention relates to a medical monitoring system with a portable electronic add-on module to be fitted to an injection appliance.

BACKGROUND

Patent application EP 2781230 describes an injection device, also referred to as an autoinjector, for the automatic dispensing of a medicinal substance using a pre-compressed dispensing or injection spring, which presses a stopper into a syringe by way of a piston rod. The movement of the stopper causes the substance to be dispensed or delivered through a needle at a distal end of the syringe. As an option, the dispensing spring or a further energy storage element can also automatically perform a piercing movement of the syringe relative to a housing of the device, in the distal direction. The injection device also comprises a needle protection sleeve that can be displaced in longitudinal direction between a proximal and distal position. The needle protection sleeve is connected to a needle protection sleeve spring as a separate drive element, which pushes the needle protection sleeve, following substance delivery, into the distal position, in which it surrounds or shields the needle at the side. A moveable stop element as a feedback device to generate an audible signal following delivery of a specific quantity of substance is accelerated to a stop by the needle protection sleeve spring. A second feedback device with a stop element accelerated by the dispensing spring signals the start of substance delivery.

Patent application EP 2182456 describes a portable electronic add-on module for fitting or snapping onto an injection appliance and for coupling to a proximal end, in particular to a dose setting button of the injection appliance. A moveable contact element in the form of a ball touches an end face of the injection appliance when the add-on module is fitted and is coupled to a piezoelectric sensor or to a pressure sensor. The sensor detects axial vibrations, and through evaluation electronics in the add-on module, identifies characteristic operating states or processes. The add-on module extends slightly in a longitudinal direction of the injection appliance, so that the latter is also held directly by the user, even when the add-on module is fitted.

The term "medicament" or "medicinal substance," in this context, includes any fluid medicinal formulation that is suitable for controlled administration by means of a cannula or hollow needle, for example, a fluid, a solution or a gel or a fine suspension containing one or more active medicinal substances. In other words, a medicament can be a composition with a single active substance or a premixed or co-formulated composition of several active substances from one single container. The term includes, in particular, drugs such as peptides (e.g. insulins, insulin-containing medicaments, preparations containing GLP-1 as well as derived or analog preparations), proteins and hormones, biologically obtained or active substances, hormone- or genetically based active substances, nutritional formulations, enzymes and other substances, both in solid (suspended) or fluid form. The term also includes polysaccharides, vaccines, DNA and RNA or oligonucleotides, antibodies or parts of antibodies, as well as suitable basic, auxiliary and carrier substances.

SUMMARY OF THE INVENTION

The task of the invention is to create a simple and cost-effective way of monitoring or controlling correct execution of an injection procedure performed by an automatic injection appliance and to pass on the injection-relevant data. It is a further task of the invention to facilitate the reliable interaction of components, appliances and systems for generating, collecting and distributing data in connection with the use of injection appliances.

This problem is solved with the help of an electronic add-on module, which is detachably attached or fitted, prior to injection, to an automatic injection appliance having a longitudinal axis, which connects a proximal end and a distal or piercing end of the injection appliance. According to the invention, the add-on module comprises a force sensor to measure a time-variable axial force component that is exerted on or transmitted to the attached add-on module in the direction of the longitudinal axis by the injection appliance during an injection procedure. According to the invention, the add-on module comprises a grip, or a preferred grip position for gripping and holding the injection appliance and the add-on module, or rather the add-on module and the injection appliance used. The grip can be an ergonomically pre-formed part of a module housing of the add-on module for gripping the injection appliance by the user with one hand, so that all other areas of the add-on module and the injection appliance that are visible in the fitted state appear to a user to be distinctly less suitable for gripping. A user who grips the injection appliance exclusively by the grip of the fitted add-on module cannot introduce any forces directly to the injection appliance or disperse them away from the injection appliance. In a state of static equilibrium, in particular, comparable axial forces are transmitted at the injection point and via the add-on module to the injection appliance, so that the force sensor in the add-on module cannot only detect the vibration of the injection appliance but also measure a constant or only gradually changing axial introduction of force by the user that produces no acceleration.

In a preferred embodiment of the invention, the add-on module comprises a sleeve-shaped module housing with an appliance holder or opening, into which the injection appliance is inserted prior to the start of injection and which, in its assembled state, at least partially surrounds the injection appliance. The grip is likewise part of the module housing and surrounds the appliance holder. In the longitudinal direction, the grip has an extension of at least half a user's hand width, in particular an extension of at least 5 cm or at least 8 cm. The grip is therefore provided radially on the outside of the appliance holder, resulting in a more compact shape than an attachment to the add-on module extending axially or to the side beyond the injection appliance. What is preferred is a clear width of the appliance holder, at least in the grip area, that is somewhat larger than the outer diameter of the injection appliance, so that even during maximum grip pressure, the appliance holder is not pressed onto the injection appliance and no additional frictional or holding forces can be transmitted in the longitudinal direction via the appliance holder between the injection appliance and add-on module, bypassing the force sensor.

In a further preferred embodiment, the add-on module has a detachable holding mechanism, which when fitted limits or even renders impossible any movement of the add-on module relative to the injection appliance in the direction of the longitudinal axis. By limiting the relative movement in the axial direction, the forces acting on the force sensor in proximal direction during injection can be limited. The holding mechanism ensures that that the injection appliance and add-on module cannot be uncoupled by accident, and the force peaks acting in a distal direction on the add-on module when the needle protection cap is removed can be dispersed through the add-on module.

In an advantageous variant, the add-on module has evaluation electronics configured to identify processes in the injection appliance or states of the injection appliance during an injection procedure, based on force sensor measurements, based in particular on distinct changes in axial force brought about by movements of the user or by a released drive mechanism. For example, the detection of an increase in the measured axial force component to a value that does not fall short of a minimum holding force during a specific minimal injection time and a subsequent drop in axial force to zero can be identified by the evaluation electronics as force applied by a user between the piercing process and removal of the injection appliance, with corresponding movement of a needle protection sleeve together with the application of pressure by a corresponding needle protection sleeve spring. Furthermore, overlapping movements of components of the injection appliance, such as rotating a sleeve or deflecting a snap lock for locking or unlocking, can result in an identifiable, time-limited rise or fall in the axial force measured.

In a further development of this advantageous variant, brief impulses of a few milliseconds duration and resulting from automatic, spring-driven movements of a stop element of the injection appliance to signal the start or end of dispense are registered or established. The measured impulses can, for example, correspond to rapidly subsiding oscillations or vibrations of the injection appliance in relation to the add-on module. In particular, the start of dispense is identified by a correlating measurement of a rapid rise in axial force to a holding force value and of a clear impetus, while the end of dispense is identified by measuring an impetus in combination with a constant axial holding force. Signaling preferably comprises an unbraked acceleration phase of the stop element and a subsequent stop or impact of the stop element to stimulate oscillation in the injection appliance, which can be primarily perceived by the user as an acoustic or tactile click signal and which, in addition, can also be measured by a suitably placed axial force sensor.

In an advantageous further development, a brief impetus signal from the force sensor is filtered and compared in a comparator or a comparison circuit with a first and preferably a second or further threshold value, and transferred to a multi-value, in particular a bi- or trivalent discrete event pattern in the comparator output signal. If such an event pattern coincides with a predetermined or stored basic pattern, which characterizes a certain basic event, the original impetus signal will be identified as belonging to the specific basic event. What is therefore exploited is that a basic event, for example a stop of a stop element to signal the start or end of dispense, has a characteristic multi-value basic pattern in the axial force output signal of the comparator, which is found in each event pattern of a single registered stop event.

In an alternative further development of the advantageous variant, the add-on module has a microphone or acoustic sensor to measure an acoustic signal during the injection procedure, in particular from oscillations of the injection appliance transmitted by air. The evaluation electronics identify the event, in this case, based on the measurement of the microphone and of the force sensor. For example, a start of dispense is identified by a correlated measurement of a rapid rise of axial force to a holding force value and of a clear acoustic signal, while an end of dispense is determined by measuring a clear acoustic signal together with a constant axial holding force.

As alternatives to the microphone, a single or multiple axis acceleration sensor or gyroscope can be used. For these alternatives, as also in the case of the microphone, positioning of the sensor in the add-on module is less critical compared with the force sensor, which is dependent on a contact surface with the injection appliance. In these further developments, an axial and in particular constant minimum force of the user on the injection appliance is continuously measured by the add-on module on the one hand, and on the other, a second measurement is performed by a type of sensor that is different from the force sensor, where both measurements are jointly evaluated to identify the event.

A state of the injection appliance or an injection procedure can therefore be determined by the add-on module solely on the basis of measurements of the axial force sensor, optionally supplemented by measurements of a second sensor. In fact, complicated detection of a set or dispensed dose is in many cases neither possible nor necessary for meaningful determination of the state or process. An injection process can be classified as correctly performed on the basis of the three events: piercing/start of dispensing, end of dispensing, and removal of the appliance. If the sequence of these events or a period of time in between them do not correspond to expectations, a corresponding message can be generated by the add-on module.

An add-on module according to the invention can be repeatedly used in an advantageous way to monitor the use or deployment of automatic one-way injection appliances or auto-injectors. The add-on module is particularly suitable for retrofit use in existing injection appliances that are not available for adjustment or modification. In this configuration, no sensors are provided in the injection appliance to record or process sensor data about the operation of the appliance, nor is there an intercommunications interface to transfer these data to a receiver. Consequently, the force sensors in the add-on device must be designed and positioned in such a way that they can detect changes in state or primary signals from within the injection appliance.

In a further embodiment of the invention, the add-on module comprises a communications unit for wireless communication with a mobile device, for example, a mobile phone or smartphone, and/or an optical, acoustic or tactile status indicator. A displayed state or status of the system can include a status of the injection appliance, a status of the add-on module, or a status of a current or completed injection procedure. The status indicator can be kept simple and be limited to a few LEDs, for example, in traffic light colours and/or an acoustic signal generator to generate non-speech sounds or melodies. This is particularly advantageous in combination with advanced graphic display possibilities and voice output possibilities of a Smartphone, because the Smartphone, which is wirelessly coupled to the add-on module, takes over refined communication with the user that goes beyond any status display. The status information can include an indication concerning the sequence of a holding or waiting time that the user must wait for following completion of dispensing before the injection appliance can be safety removed from the injection site. Simply measuring the time elapsed since the established end of dispensing and comparing it with a target time allows the user to determine time when it is safe to remove the injection appliance. This can be done both by an add-on module with a time-recording function and by a mobile device with real-time event transmission coupled to an add-on module.

For the expert in the field, further embodiments and developments are directly and obviously evident and result from combinations of the examples described, or combinations of the examples described with the general expertise in the field.

BRIEF DESCRIPTION OF THE DRAWINGS

The following preferred embodiments of the invention are described below in connection with the attached figures. These are to highlight the fundamental possibilities of the invention and must not be interpreted in a restrictive manner.

DETAILED DESCRIPTION

Figure 1A:
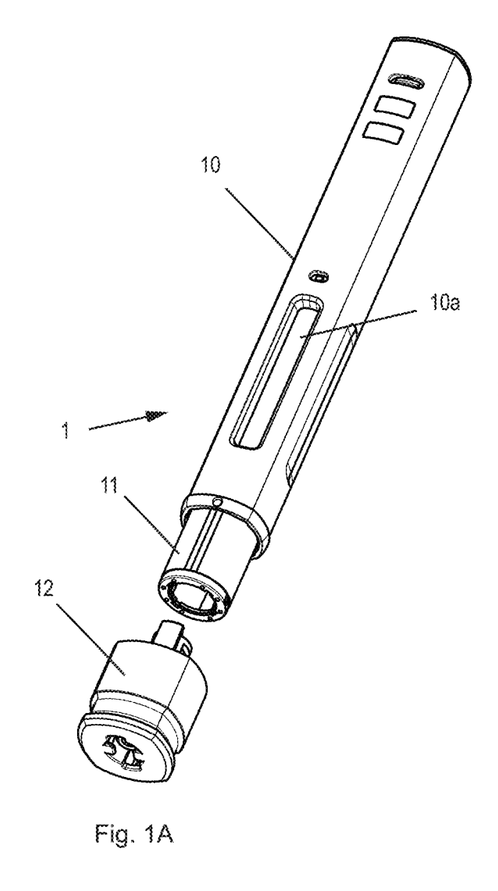
FIGS. 1A-1B show an injection system with an injection appliance and an add-on module.
Figure 1B:
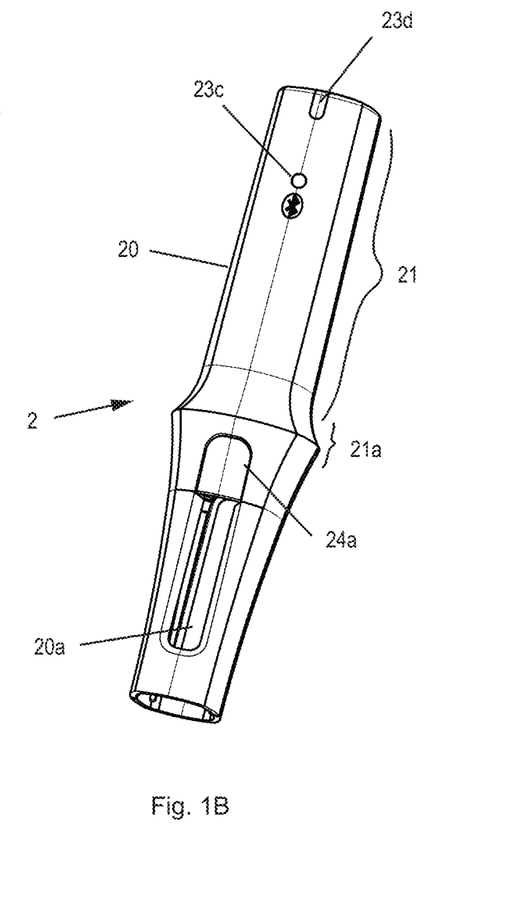
Figure 1C:
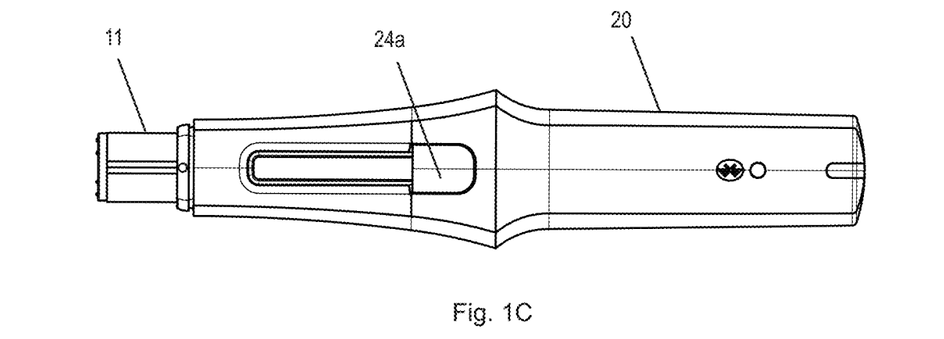
FIG. 1C shows these fitted together.

FIGS. 1A-1C show an injection system with an injection appliance 1 and an add-on module 2, both in a separate state (FIG. 1A-1B) and in a fitted, mounted, combined or coupled state (FIG. 1C). The injection appliance has a long device housing 10 that is symmetrical around a longitudinal axis, and a needle protection sleeve 11 that can be displaced between a first position shielding a needle of the injection appliance (shown in FIG. 1) and a second position exposing the needle. A needle protection cap remover 12 in its delivered state is fitted to a distal end of an injection appliance and, prior to injection, has to be removed or pulled off together with a needle protection cap that mechanically protects the needle. The add-on module has a long, sleeve-shaped module housing 20 with a hollow space as an appliance holder for the injection appliance, said appliance holder being matched to the external shape of the appliance housing, so that the injection appliance can be inserted into the add-on module for coupling purposes. The add-on module has a release button 24a of a holding device, an optical status display 23c, 23d for a visual feedback to the user, and side openings 20a, which, in the fitted state, are aligned to windows 10a in the appliance housing and make it possible to see a substance that is stored in the injection appliance. Alternatively, the add-on module can also be distinctly shorter than the injection appliance, in other words, only about two thirds or just about half as long. On the outside, the module housing has a grip 21 with a slightly concave grip position, which comprises a slightly raised portion 21a as the distal grip limit or an area of increased diameter in order to make easier absorption of user force in the distal direction.

At the start of the injection, the distal end of the injection appliance, i.e., the needle protection sleeve, is pressed onto the injection site by the user so that the needle protection sleeve is inserted, under compression of the needle protection sleeve spring, in a proximal direction, into the injection appliance, and at the same time, the needle penetrates the injection point. In order to guarantee that in every case the user transmits the force to the injection appliance throughout the injection process, including release and execution of dispensing by means of the add-on module, the add-on module is developed as a sleeve over a major part of the injection appliance. The injection appliance can therefore not be unintentionally held. A clear width or an internal diameter of the appliance holder, except for at the holding mechanism, is larger, at least in the area of the grip, by an amount of a few tenths of a millimeter above the manufacturing tolerances than an external diameter of the injection appliance. In other words, the add-on module has some radial play in relation to the injection appliance, except for at the holding mechanism, so that they can move without friction in relation to one another and the entire force is transmitted through the force sensor.

Figure 2:
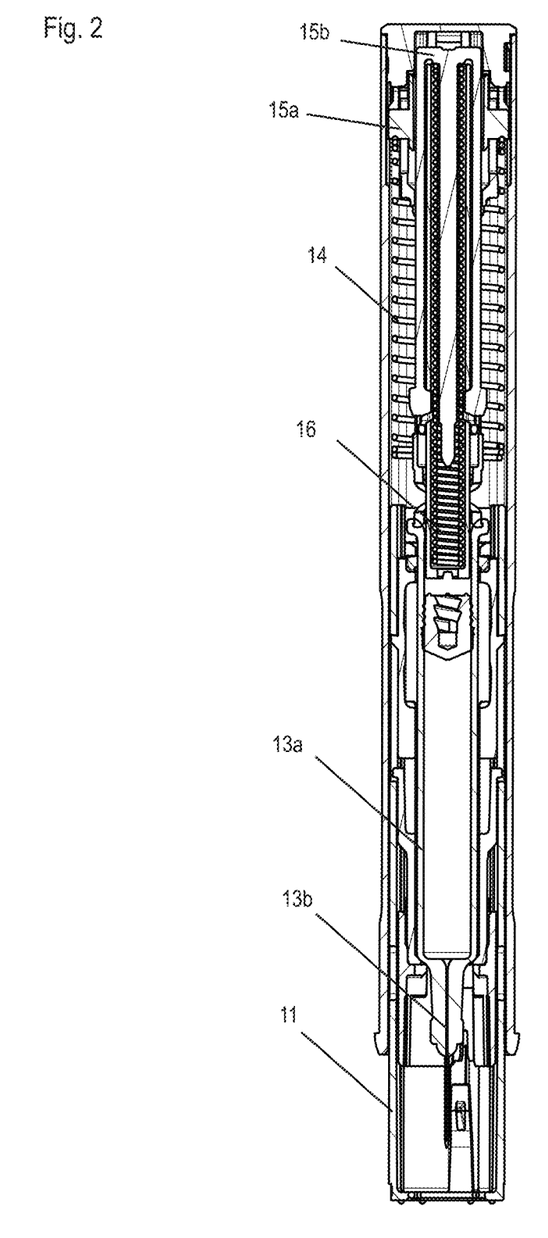
FIG. 2 shows an injection device in longitudinal section.

FIG. 2 shows the longitudinal section of an injection device in a state prior to injection, in which a syringe 13a with needle 13b filled with a substance to be dispensed is used. A proximal end of a hollow cylindrical needle protection sleeve 11 is in contact with a rigid locking sleeve, which in turn is adjacent to a needle protection sleeve spring 14. At the proximal end of the needle protection sleeve spring, an initial stop element or click element 15a is provided to mark the end of dispensing (end of injection, EOI). At the start of dispensing, a piston rod is connected to the first stop element by way of cams so that the first stop element can be moved forward by a small stroke at the start of dispensing, thereby further compressing the needle protection sleeve spring. Following complete dispensing of the substance and conclusion of the forward movement of the piston rod, the first stop element is released and accelerated proximally backward by the needle protection sleeve spring, where it strikes an end cap and generates a clicking sound which can be clearly heard by the user, and a noticeable knock. A second stop element 15b or click element is provided to mark the start of dispensing (start of injection—SOI). Initially, a click pin is interlocked with the piston rod to prevent any relative movement. When triggering dispensing by proximally displacing the needle protection sleeve and the locking sleeve, the piston rod and click pin are released and are forced apart by a pre-compressed injection spring 16. This movement by the click pin is transmitted to the second stop element, so that the proximal end of the second stop element strikes the end cap and generates a clearly audible clicking sound and a force surge or impulse.

As an alternative to the simultaneous insertion of the needle protection sleeve and needle piercing, a syringe that is slidably mounted in the injection appliance and that is surrounded in its delivered state, including the needle point, by the appliance housing, can be moved by the force of a piercing and/or dispensing spring relative to the appliance housing. This automatic piercing movement is triggered following a partial or complete insertion of the needle protection sleeve into the injection appliance. The impact of the accelerated syringe on a stop element likewise causes a distinct impetus followed by a roughly constant holding or dispensing force. The preceding insert movement of the needle protection sleeve with simultaneous compression of the needle protection sleeve spring can take place slowly and, in the case of a pre-compressed needle protection sleeve spring, possibly only after the spring biasing force has been overcome. The movement may result in a continuous rise in measured axial force, possibly by applying a minimal unlocking or injection blocking force that can be seen in the force curve and is superimposed on the spring compression force.

In a further embodiment, the piercing movement can also be started by a release button operated by the user.

Figure 3:
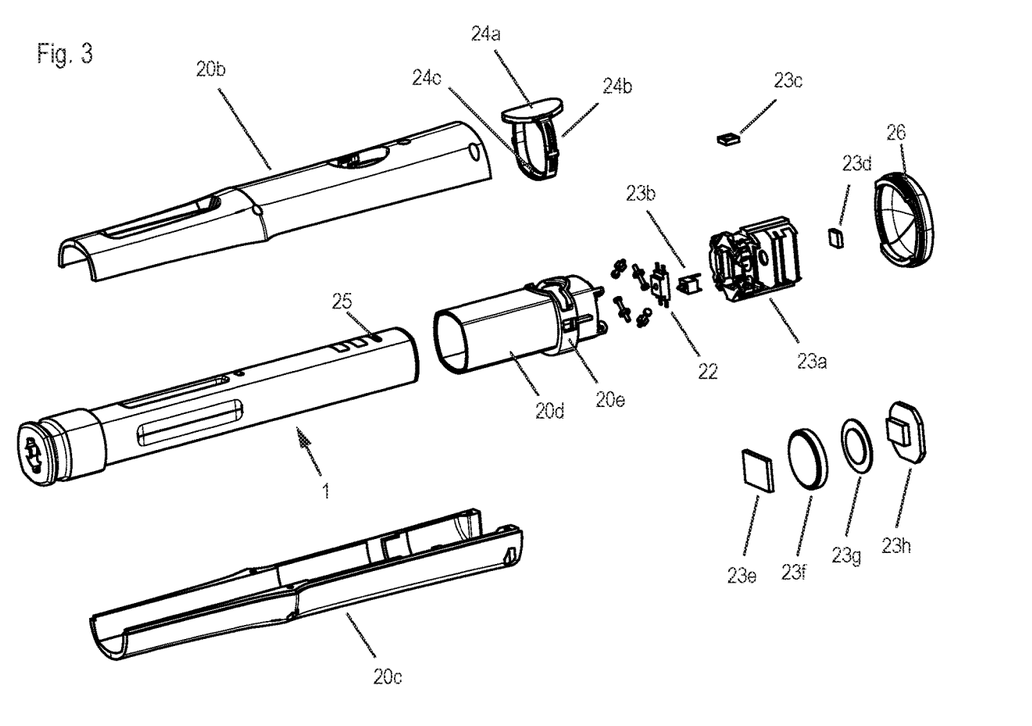
FIG. 3 shows an exploded view of an add-on module.

FIG. 3 shows an exploded view of an add-on module according to the invention. The module housing comprises a first housing half 20b and a second housing half 20c that are snapped onto a module sleeve 20d. In an electronics holder 23a, in the rear section of the add-on module, is accommodated the module electronics, comprising a force sensor 22 or a pressure sensor, a contact switch 23b to detect complete insertion of the injection appliance into the add-on module, a connection status indicator 23c to signal successful establishment of a connection to a mobile device 31 (see FIG. 8), a status display 23d with LEDs and light guides in the form of a transparent, distal sealing cap 26. Also provided are a microphone 23e, a battery 23f as energy source, a buzzer or loudspeaker 23g to generate sounds, and a communications unit 23h with a Bluetooth Low Energy (BLE) chip including an evaluation unit for signal processing and data storage. The status display may, in particular, show the following states: add-on module fitted, add-on module ready, injection running, injection ended, holding time elapsed, remove add-on module, BLE status. The status display can also emit warnings, such as add-on module incorrectly fitted, add-on module switched off because of inactivity, battery status low, reminder to remove add-on module, or even error messages such as end of injection during dispensing, ending injection during holding time.

A holding device or holding mechanism comprises an annular transfer element 24b guided in annular guide 20e of the module sleeve 20d, a holding structure or nose 24c securely fitted to the transfer element, a latching spring that moves the transfer element 24b together with a holding structure into a holding position, and a release button 24a as an operating element to move the transfer element 24b and to release the holding structure from the holding position. In the holding position, the holding structure is latched in a recess 25, such as a notch or slit in the injection appliance housing. This recess can also be used for other purposes and is ideally already available in existing injection appliances, which means that no adjustment has to be made to the injection appliance in order to use the add-on module. As an alternative to pressing on the release button and moving the transfer element perpendicularly to the longitudinal axis, the operating element can also perform a sliding movement. When the holding structure is released, the injection appliance can slide out of the add-on module in the axial direction, so that the holding mechanism makes it possible to snap the add-on module onto the injection appliance such that it can be detached. The module housing in FIG. 3 is distinguished from that in FIG. 1, in particular by the arrangement of the holding device within the grip area instead of between the grip area and the distal housing end. The holding device is therefore gripped by the user during holding, and the release button in this case is slightly recessed in the module housing so as to prevent accidental release by the user's holding hand.

The holding device may have slight play through the corresponding design of the holding structure and recess 25 in the axial direction, so that the force sensor 22 can move away from the end cap or contact surface. In this case, the force sensor 22 is not pre-stressed when the injection appliance is not placed on the injection site and the needle protection sleeve spring is not compressed. Accordingly, a signal or click at the end of dispensing following premature removal of the injection appliance may possibly no longer be detected by the force sensor, so that only acoustic identification via the microphone can contribute to the completion of the defective injection process. On the other hand, by force-fit snapping in of the holding structure of the add-on module into the recess 25 of the injection appliance, the force sensor can also be pre-loaded or pre-stressed. In one such case, a pre-stress path in the module housing between holding device and force sensor is accordingly pre-stressed in tension and, under certain circumstances, only external axial forces can be observed at the force sensor above a certain pre-stress value. For example, an axial force sensor in contact with the proximal face of the injection appliance initially measures the pre-stress value as well as any small user force, which is dispersed to the rear, for example, by avoiding the pre-stress path. On the other hand, in the preferred arrangement of the grip as part of the module housing enclosing the appliance holder, the axial force of the user is at least partially led via the pre-stress path to the force sensor. As a result, the tension load in the pre-stress path is initially reduced, and only user forces above a minimum value that does not exceed the pre-stressing force are measured by the force sensor in addition to the pre-stressing force.

In the embodiment shown, the axial force sensor within the add-on module in its fitted state comes to rest against the proximal or rear end of the injection appliance. In other words, it makes contact with a proximal surface or end cap of the injection appliance, which represents a simplification compared with a transfer of force via a contact surface provided on the side of the appliance perpendicular to the axis, in other words, for example, via a proximal annular face of a surrounding flange or of a section thereof. Likewise, a diversion of the axial force by means of moving components on the add-on module in a direction that deviates from the longitudinal direction is conceivable, for example, for non-axial positioning of the force sensor.

Suitable force sensors are based on a piezo-resistive effect, in other words, on a change in the specific electrical resistance of a conductor when mechanically deformed. In the case of the Honeywell FSS series force sensors, the resistance of piezo-resistances incorporated in a silicon measuring element increase if said piezo-resistances are bent by force, which can be measured by a resistance bridge. The sensor transmits any force applied between zero and 20 N via a high-grade steel ball directly to the silicon measuring element, where the ball is moved by a maximum stroke of 50 micrometers. Alternative force sensors for measuring holding forces comprise strain gauges fitted to cantilever beams or FSR (Force Sensing Resistor) pressure sensors.

The evaluation unit can be integrated in the communications unit 23h or can be provided as an independent chip on the electronics holder. The evaluation unit processes the signals of the force sensor 22 and any further sensors provided, provides a time stamp, and determines consolidated injection information from the processed signals and relevant time stamps. The injection information includes at least information that an injection has been successfully carried out at a specific time, or what faulty actions have possibly been carried out. Such information is stored in a memory unit in the add-on module and/or forwarded via the communications unit 23h. The memory unit can also store identification data of the user or the add-on module.

In order to save energy, the contact switch 23b can also operate as an activation element to activate the add-on module from a power-saving mode. In addition or as an alternative, the energy source can be recharged, for which purpose the add-on module has a suitable plug connector or is provided with a charging station for inductive energy transfer. The charging station can only accommodate the add-on module or the add-on module with attached injection appliance and can also be used by other chargeable appliances of the user. An intelligent charging station can act as a base station and have additional functionalities, for example measuring the temperature of the attached injection appliance and/or of the medicament that it contains. If the injection appliance is placed in the charging unit following storage in the fridge and prior to use, such a temperature measurement at the injection appliance can issue a signal as soon as a minimum temperature for administering the medicament is reached. During the warming process, the energy source of the add-on module can also be recharged without any further intervention by the user. By way of a further communications interface, the intelligent charging station can also provide time and date information in order to synchronize a clock on the add-on module, or can adopt the consolidated injection information as a fallback level to the mobile appliance, as described below.

Figure 4:
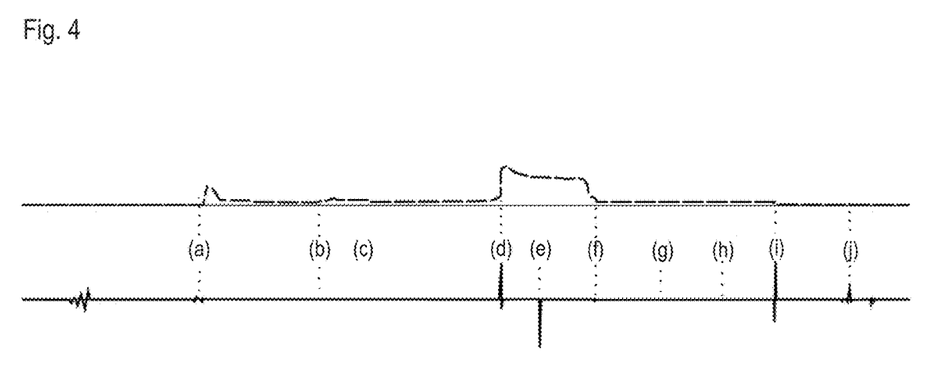
FIG. 4 shows the measured signals of a force sensor (top) and a microphone (bottom) in the add-on module.

FIG. 4 shows the signals from a piezo-resistive force sensor (top) and an electret microphone (bottom) measured during a complete injection procedure lasting 20 seconds. The following events are assigned to the signals: (a) connecting add-on module and injection appliance, (b) removing the needle protection cap from the injection appliance, (c) moving/tilting the injection appliance to the injection site, (d) start of dispensing (start of injection—SOI), (e) end of dispensing (end of injection—EOI), (f) removing the injection appliance from the injection site, (g) placing the injection appliance in a horizontal position, (h) setting aside the injection appliance, (i) lifting and dropping the injection appliance, (j) removing the injection appliance from add-on module. The drop in force of the measured axial force when removing or withdrawing the injection appliance from the injection site (event f) is more continuous than when piercing (event d) and follows the releasing needle protection sleeve spring, possibly with formation of a peak superimposing the edge, caused by a movement of a needle protection sleeve locking mechanism.

States, processes and events in the injection appliance and during the injection process can be identified, as follows, by way of example, by combinational interlinking of the information from the force sensor and the microphone. In order to detect a start click, the combination of a clear acoustic peak and an increase in force (remaining on the force plateau) is required. In order to detect an end click, the combination of a clear acoustic peak and a consistently high force is demanded. Removal of the injection appliance together with the add-on module from the injection site is detected by the reduction in force after the end click. If the injection appliance is removed from the injection site before the end click or even during the required holding time, this can be detected by the premature drop in force.

Figure 5:
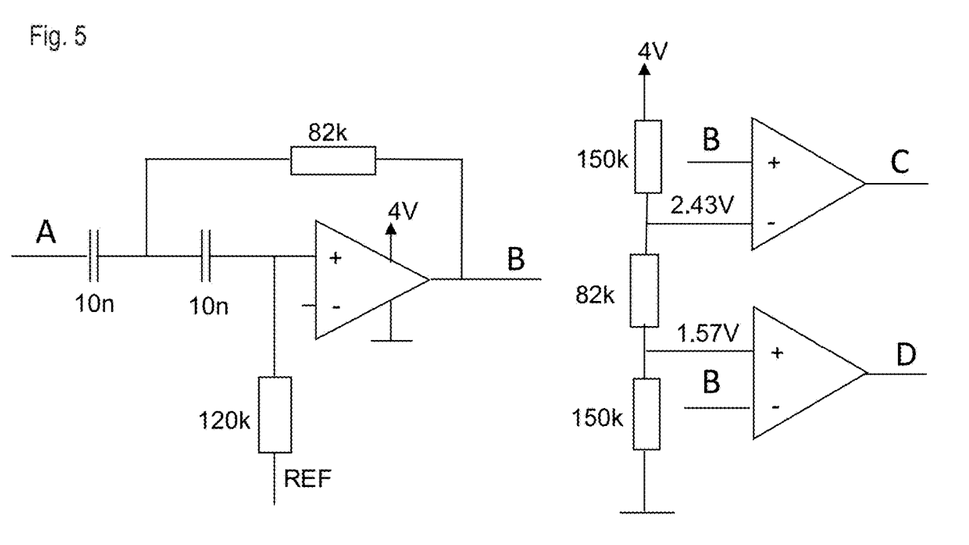
FIG. 5 shows a diagram of the evaluation electronics of an add-on module.

FIG. 5 shows a diagram of evaluation electronics as part of the evaluation unit, to be applied to an input signal A measured by the force sensor. The low frequency signal components are filtered out in a high-pass filter with a cutoff limit of 200 Hz (FIG. 5, left). The filtered signal comprises both positive and negative peaks in line with the deviations in the impetus signal compared with a holding force plateau. In order to avoid negative voltage values, the output signal of the filter is raised to an offset of 2 V (half the supply voltage). The resulting signal B is fed to a comparator (FIG. 5, right), which compares the analog signal with an upper and lower limit value of an amplitude window and converts it into pulses. If the signal prepared in this way exceeds the upper limit value, then an initial comparator output value C, for example a pulse of plus 1 V, is emitted, or a corresponding bit or character is set. If the signal falls short of the lower limit value, then a second comparator output value D, for example a pulse of minus 1 V, is generated. Subsequently, a trivalent discrete event pattern is generated as a consequence of positive and negative pulses of different length, separated by a neutral or mid-value pulse of random length.

The evaluation electronics can be implemented in an analog, digital or mixed way. For example, the high-pass-filtered analog sensor signal is conveyed to a microprocessor, where it is converted into a digital signal and fed to the digital comparator function programmed in the microprocessor memory. A scanning rate for digitizing the impetus signal must be selected according to Nyquist. For an impetus signal corresponding to an acoustic click sound with a frequency spectrum of up to 5 kHz, scanning every 20 microseconds is therefore appropriate.

Figure 6A:
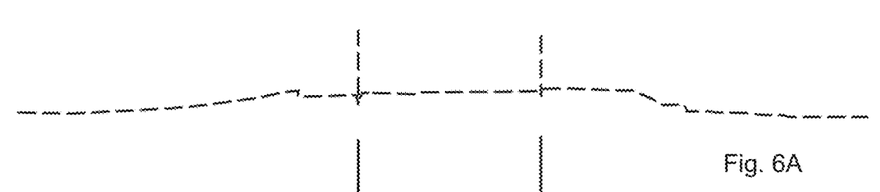
FIG. 6A shows a signal measured through a force sensor and FIG. 6B shows it as filtered.
Figure 6B:
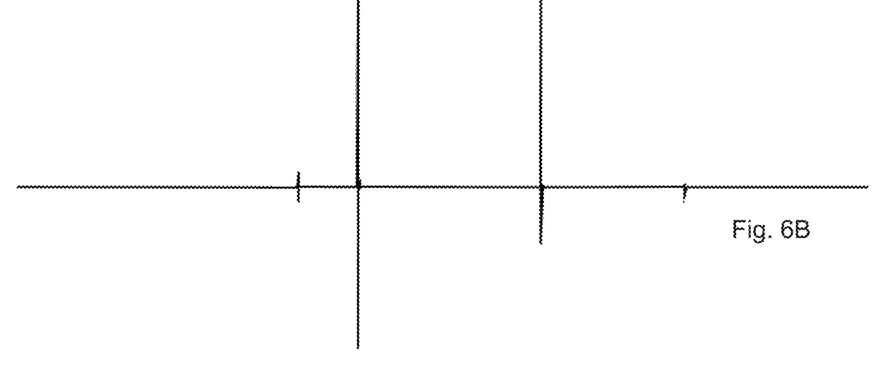

FIG. 6 shows an input signal A measured by a force sensor at the input of a filter, as well as the filtered signal B at the input of a comparator generated by filtering signal A. The entire process depicted lasts for 5 seconds. Accordingly, the impetus signals at the start and end of dispensing, corresponding to a start-of-injection and end-of-injection click, can only be detected as narrow peaks.

Figures 7A, 7B, 7C:
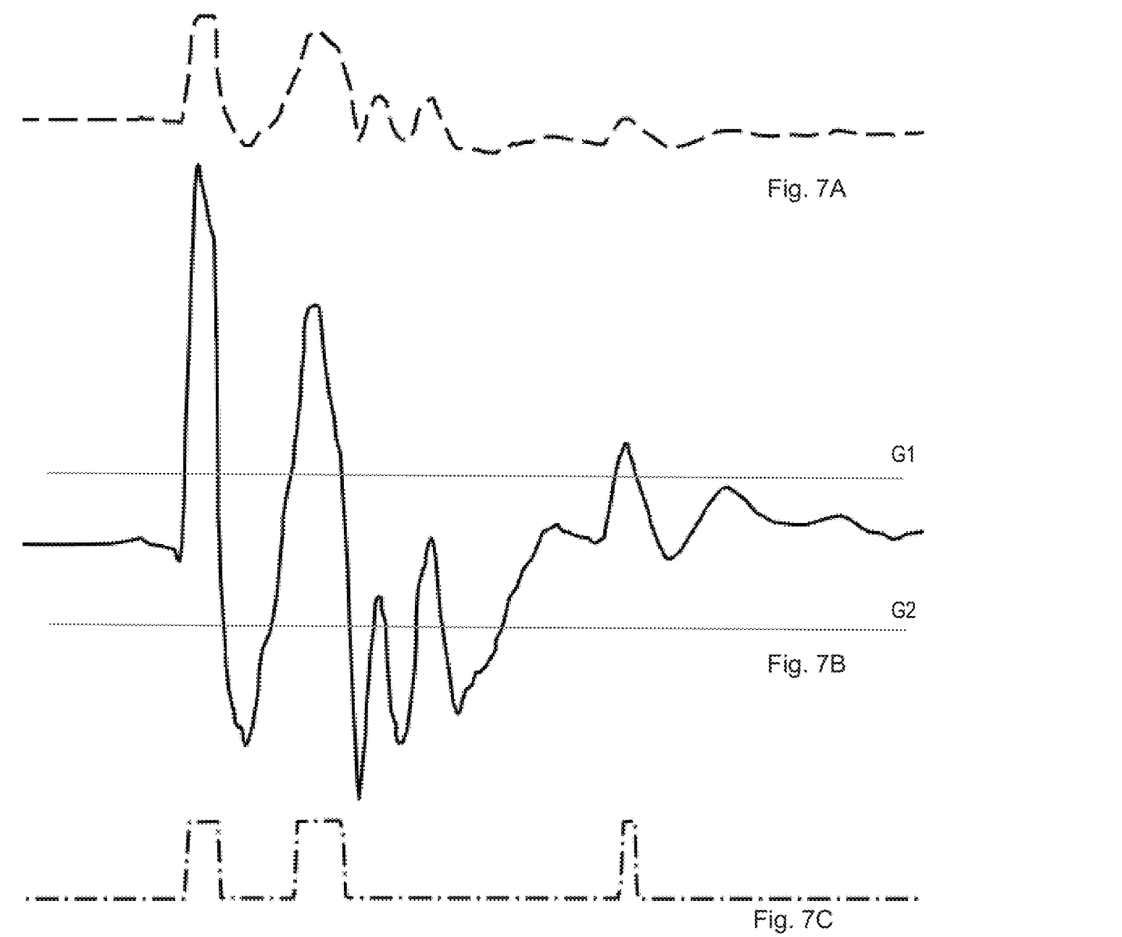
FIGS. 7A-7E show an event pattern formation from an impetus signal.
Figure 7D:
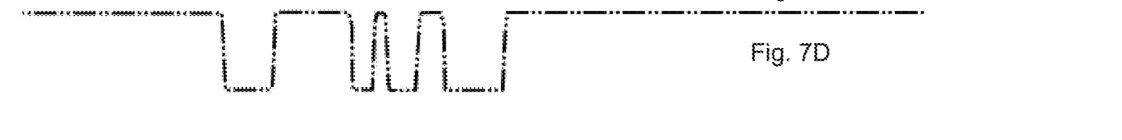
Figure 7E:
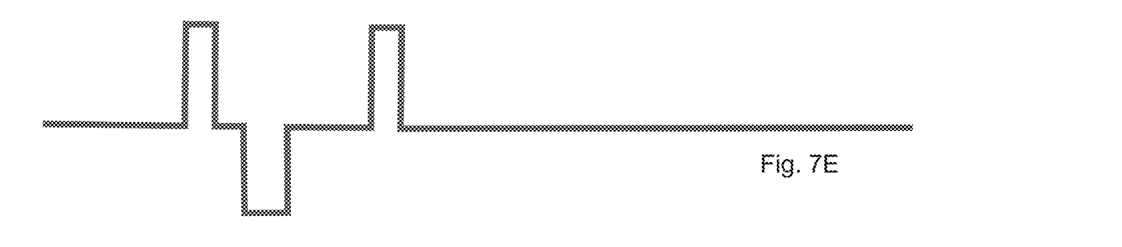

FIG. 7 shows an example of event pattern formation for the impetus signal at the start of dispensing in FIG. 6, which undergoes resolution over a period of 8 milliseconds. The unfiltered signal A and the filtered signal B show correspondingly more structure. By comparing signal B with an initial limit or threshold value shown by the upper horizontal line G1, an initial comparator output signal C is generated with three pulses of different length. By comparing signal B with a second limit or threshold value shown by the bottom horizontal line G2, a second comparator output signal D is generated, in this case comprising a sequence of four pulses of different length. The consequence of the second pulses is shown as negative values for the sake of better legibility. The resulting event pattern from the selected pulse with the two components C and D coincides with the characteristic basic pattern or the signature of a start click, shown by the curve E, to the extent that the three pulses of the basic pattern are completely within pulses of the event pattern in terms of time. Accordingly, the impetus signal is identified as coming from a start click. The limit values G and the relevant basic pattern E are preferably determined by an iterative procedure with repeated recording and analysis of impetuses of known origin. The selected limit values then ideally result in minimum scattering in the event patterns and hence to a high degree of reproducibility. The algorithm introduced can successfully identify or rule out previous actions and incorrect handling, such as lifting the add-on module, assembling the add-on module, removing the needle protection, turning, dropping, loud ambient noises, and shaky holding as impetuses that are not relevant to injecting and do not coincide with any basic signal.

Figure 8:
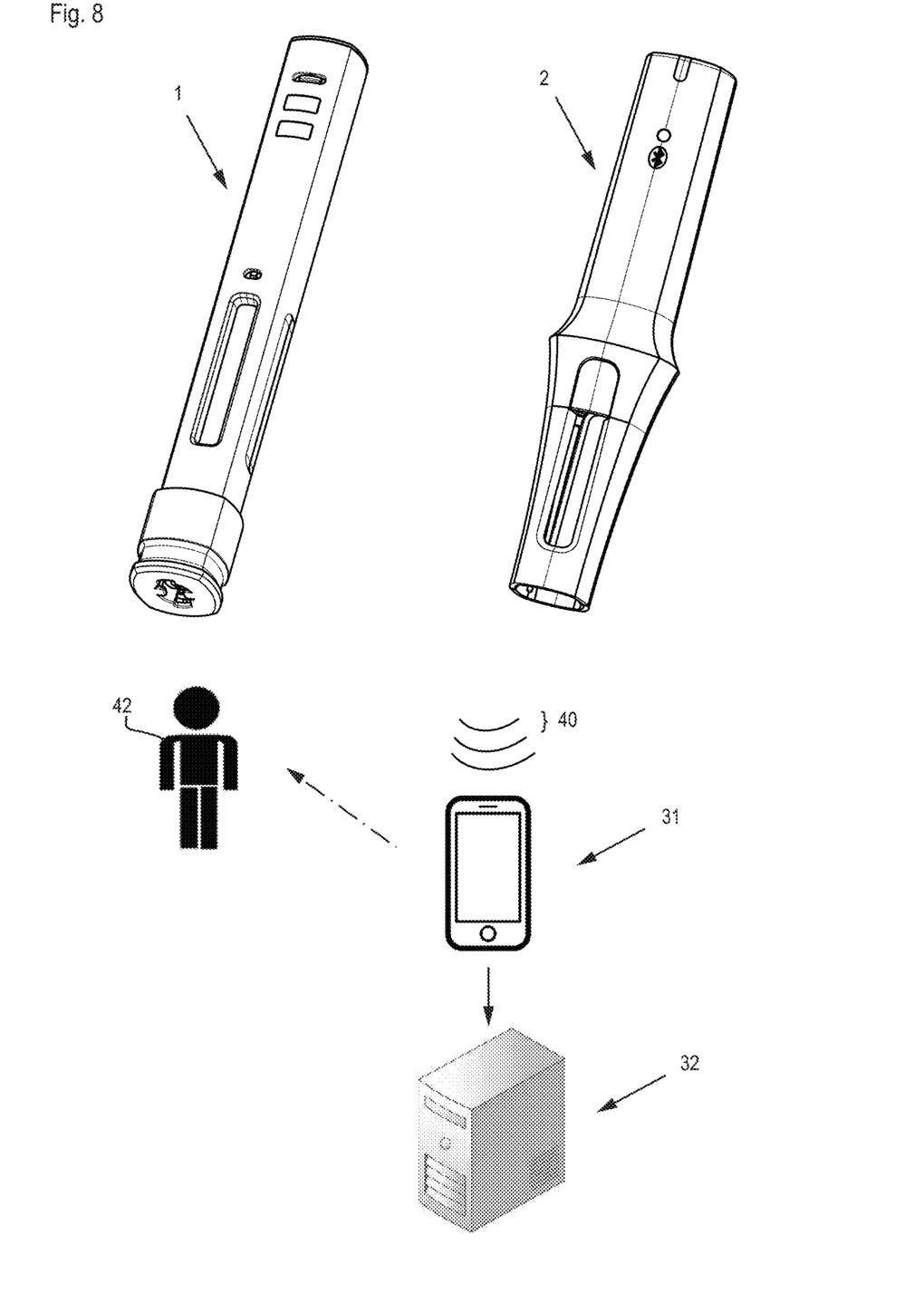
FIG. 8 shows an enlarged medical monitoring system.

FIG. 8 shows an expanded medical monitoring system with an injection appliance 1, an add-on module 2, a mobile display and output unit 31, which can communicate wirelessly with the add-on module and an optional, fixed data processing system based on delocalized data storage (cloud computing), or expert system 32. The add-on module transmits data (indicated at signal 40) from an injection process and/or consolidated injection information wirelessly to a compatible mobile device, for example, to a smartphone having a special application or to a duly configured portable computer.

The mobile device must be initially set up and configured, for example, by installing an application and registering the user 42. This can be done by a patient data card that transcribes all the relevant data onto the mobile device 31 using near-field radio communication (NFC) or optical QR codes. If the mobile device 31 is located within range of the add-on module, then this data transmission can take place in real time during an injection procedure or only once it is completed. In the first case, the mobile device 31 can issue instructions to the user 42 in real time and thereby guide the user through the next steps. In all events, the injection information may also be stored in the add-on module 2 and only transmitted later in consolidated form. The data received from the mobile device 31 can be supplemented by the user 42, for example by indicating the injection site, and are passed on in a suitable way to the expert system. The latter stores the data and provides patients, medical staff and health insurers with targeted information, and in this way assists the user of the injection appliance in following a treatment plan.

REFERENCE LIST

1 Injection appliance
10 Appliance housing
10*a* Window
11 Needle protection sleeve
12 Needle protection cap remover
13*a* Syringe
13*b* Needle
14 Needle protection sleeve spring
15*a*, 15*b* Stop element
16 Dispensing spring
2 Add-on module
20 Module housing
20*a* Opening
20*b*, 20*c* Housing halves
20*d* Module sleeve
21 Grip
21*a* Grip limit
22 Force sensor
23*a* Electronics holder
23*b* Contact switch
23*c* Connection display
23*d* Status display
23*e* Microphone
23*f* Battery
23*g* Buzzer
23*h* Communications unit
24*a* Release button
24*b* Transfer element
25 Recess
26 Add-on cap
31 Mobile device
32 Data processing system
40 Transmitted signal
42 User
20*d* module sleeve; 20*e* annular guide; 24*c* holding structure or nose.

What is claimed is:

1. Injection system with an injection appliance and an add-on module for monitoring an injection procedure of the injection appliance, the add-on module comprising:
   an appliance holder comprising a holding mechanism of the appliance holder for detachably fitting the add-on module to the injection appliance;
   a force sensor for measuring a time-variable force component in the direction of a longitudinal axis exerted on or transmitted to the add-on module during the injection procedure; and
   a grip for facilitating a user to hold the fitted add-on module, said grip being provided radially outside the appliance holder and configured with the appliance holder, except for at the holding mechanism, having a clear width or internal diameter such that during grip pressure, the appliance holder is not pressed onto the injection appliance and no additional frictional or holding forces can be directly transmitted in the longitudinal direction via the appliance holder between the injection appliance and the add-on module, bypassing the force sensor;
   and wherein the injection appliance has a needle protection sleeve spring, which is configured to be compressed during a piercing process, wherein the add-on module is configured to identify the piercing process from an increase in an axial force measured by the force sensor to a value that is at least approximately constant and brought about by the compressed needle protection sleeve spring.

2. Injection system according to claim 1, wherein the needle protection sleeve spring accelerates a stop element at the end of dispensing and the add-on module is configured to identify a stop of the accelerated stop element from an impetus detected by the force sensor.

3. Injection system according to claim 2, wherein the appliance holder at least partially encloses the injection appliance in a fitted state, and the grip encloses the appliance holder and, in the direction of the longitudinal axis, has an extension of at least 5 cm.

4. Injection system according to claim 2, wherein the holding mechanism of the appliance holder fixes the injection appliance in a fitted state in the direction of the longitudinal axis, the holding mechanism comprising an annular transfer element with a nose latched into a recess of the injection appliance.

5. Injection system according to claim 2, wherein the holding mechanism of the appliance holder fixes the injection appliance when in a fitted state in the direction of the longitudinal axis, the holding mechanism comprising an annular transfer element with a nose latchable into an injection appliance recess and the appliance holder at least partially surrounds the injection appliance, with radial play in relation to the injection appliance, except for at the holding mechanism so that the injection appliance and the appliance holder can move without friction in relation to one another.

6. Injection system according to claim 2, further comprising evaluation electronics to evaluate measurements of the force sensor for the purpose of identifying a procedure or a state of the injection appliance.

7. Injection system according to claim 6, further comprising:
   a second sensor in the form of a microphone to measure an acoustic signal from the injection procedure, and the evaluation electronics are configured to identify a movement of the stop element of the injection appliance signaling the start or end of dispensing based on the microphone measurements.

\* \* \* \* \*